Feb. 16, 1937. L. BURBANK Plant Pat. 235
ROSE
Filed July 28, 1936
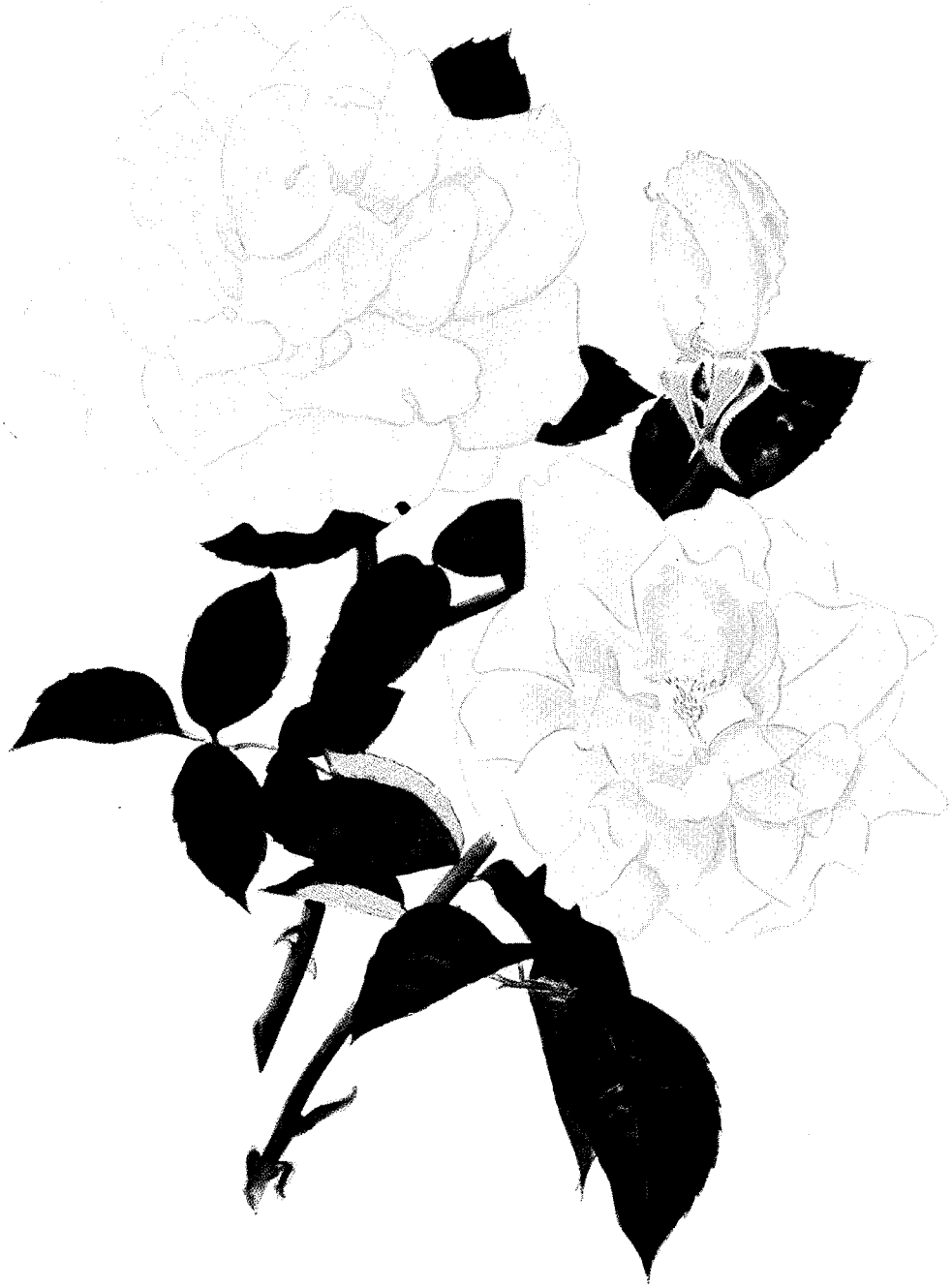
Inventor
Elizabeth Waters Burbank
Executrix of the estate of
Luther Burbank, Deceased
By Robb & Robb Attorneys Patented Feb. 16, 1937 Plant Pat. 235

UNITED STATES PATENT OFFICE

235

ROSE

Luther Burbank, deceased, late of Santa Rosa, Calif., by Elizabeth Waters Burbank, executrix, Santa Rosa, Calif., assignor to Stark Bro's Nurseries & Orchards Company, Louisiana, Mo.

Application July 28, 1936, Serial No. 93,107

1 Claim. (Cl. 47—61)

The present invention appertains to a new variety of yellow hybrid tea rose characterized primarily by the novel color, formation, fragrance and fastness of color of its flower, all of which are quite unusual although desirable in roses of this general class. Color names not asterisked refer to the drawing and the ordinary dictionary definitions.

The new creation, which has been asexually reproduced, is found by tests to possess permanent characteristics. It bears exceptionally long pointed graceful buds which are rosy buff in color, blending to rosy copper near the center and deep canary yellow at the base. Upon opening of the bud in the development of the flower, there is produced a large, open-faced, semi-double bloom having the inner row of petals curving inward concealing the stamens, thereby giving it a more double appearance than it actually possesses. The delightful tea rose fragrance of the flower is prominent. Unlike most roses of this class, the color of the flowers is lasting and does not fade—an important desideratum in any rose.

The nearest known approach to this new rose is the Duchess of Wellington. However, it can readily be distinguished from it. This well known Duchess of Wellington variety produces flowers with more of a light pink tint fading out to a whitish pink as the flower develops. On the other hand, the flower of the new variety possesses a predominate canary or sulphur yellow color. In the bud, this color blends to a rosy buff or shell pink on the outside at the top of the petals. In the open flower, the formation is more single than the Duchess of Wellington.

For convenience, the following summary of the most predominate characteristics of the new variety are set forth:—

Parentage:

Seedling of unknown parentage originated at Santa Rosa, California.

Bush:

*Growth.*—Strong, vigorous, divergent to spreading, some of the main stems being very heavy with spreading branches extending from them.

*Bark.*—Becomes rough, *bone brown in color, woody, with longitudinal *Verona brown ridges and markings.

*Thorns.*—Numerous, large to medium, *bister to cinnamon brown in color on oldest wood, *Vandyke red on younger wood, yellow points distinctly recurved on younger growth.

Foliage:

*Quantity.*—Abundant, persistent.

*Size.*—Medium to large.

*Leaflets.*—3 to 7 in number, oval to ovate.

*Texture.*—Medium to rather thin on new growth, moderately stiff.

*Blade.*—Flat or slightly wavy.

*Base.*—Obtuse.

*Margin.*—Rather finely double-serrate, sharp points, small alternate serrations glandular tipped, large points barbed, strongly forward. The edges and points are tinged with *Vandyke red as on new growth.

*Apex.*—Broadly acute.

*Upper surface.*—Glaucous, rather glossy when the thin bloom is removed, *ivy green in color.

*Under surface.*—Glaucous, white bloom and surface layer of white cells modifying the color effect to substantially *light grape green.

*Petiole.*—Rather slender, stiff, irregularly curved or sinuous.

*Color.*—*Deep chrysolite green.

*Upper side.*—Distinctly grooved, tinged *Vandyke red on new growth as are also the numerous glandular tipped bristles along edges of groove and on stem of leaflets and midribs.

*Under side.*—Round and set with a number of rather large sharply recurved spines, some even on midrib of terminal leaflet.

Flowers:

*Arrangement.*—Borne singly or in large open branched clusters.

*Stems.*—Medium to long, leafy, beset with stiff, sharp pointed spines ½ inch in length, 3 to 4 to each internode.

*Bark.*—Smooth, glaucous *courge green, under thin whitish bloom faintly lined with lengthwise markings of lighter green, tinged as also on new growth *Vandyke red.

*Form.*—Individual, rather short, subtended by 2 or 3 lanceolate bracts.

*Buds.*—Very large, 1½ inches in average length, and ¾ inch wide at widest part, long ovate, edges of petals crinkled and wavy, unfolding early but retaining bud-form for a long period; buds set on pedicels 3 to 5 inches in length and arranged in clusters of from 3 to 5 flowers to each cluster.

*Color.*—Tip of bud rose-buff, blending to rosy copper near center and deep canary yellow at base.

*Bloom.*—Semi-double, showy, 15 to 20 petals per bloom.

*Size and form.*—Large; outer row of petals 5 in number and when fully developed averaging 2½ inches in length and 2 inches wide, broadly cordate in shape and prominently notched at apex; inner row of petals modified, partly developed and curved inward, giving flower a more double appearance and partly concealing the stamens; open flower averaging 4 inches across and 1½ inches deep.

*Color.*—When fully developed there is some trace of pink on extreme margin of some of the petals, blending to light buff or ivory half way and lower or basal portion blending to canary yellow; inner petals of deeper canary yellow at base, blending to buff with slight pinkish tinge.

*Filaments.*—*Light cadmium in color.

*Anthers.*—Edged *deep chrome.

*Styles.*—Pale greenish silky pubescent at base, shading to *amaranth purple.

*Stigmas.*—Nearly white.

*Fragrance.*—Pronounced tea-rose type and very pleasing.

(*Ridgway's Color Standard)

Having set forth the most notable features of the invention and the distinctions from the variety which it most nearly resembles, it is apparent that the rose is clearly endowed with individual identity and is characterized truly as a new and distinct variety.

What is claimed is:

A new and distinct variety of rose as herein described characterized particularly by the color and gracefulness of form of its flower, and its exceptionally long pointed buds, as herein shown.

ELIZABETH WATERS BURBANK,
*Executrix of the Estate of Luther Burbank, Deceased.*